United States Patent [19]

Scriabine et al.

[11] 4,016,288

[45] Apr. 5, 1977

[54] COMPOSITIONS AND METHOD OF TREATING HYPERTENSION

[75] Inventors: Alexander Scriabine, Ambler; Clement A. Stone, Blue Bell, both of Pa.

[73] Assignee: Merck & Co., Inc., Rahway, N.J.

[22] Filed: Aug. 13, 1975

[21] Appl. No.: 604,292

[52] U.S. Cl. .............................. 424/309; 424/319
[51] Int. Cl.$^2$ ............... A61K 31/24; A61K 31/195
[58] Field of Search ........................... 424/319, 309

[56] References Cited

UNITED STATES PATENTS

| | | | |
|---|---|---|---|
| 3,784,703 | 1/1974 | Stone | 424/319 |
| 3,795,739 | 3/1974 | Birkmayer et al. | 424/319 |
| 3,830,827 | 8/1974 | Karady et al. | 424/319 |
| 3,839,585 | 10/1974 | Lotti et al. | 424/319 |

*Primary Examiner*—Sam Rosen
*Attorney, Agent, or Firm*—Daniel T. Szura; J. Jerome Behan

[57] ABSTRACT

The present invention relates to a novel and useful method of treatment and a composition which is used to treat hypertension. More particularly, it relates to the administration of a composition containing (A) L-α-hydrazino-α-loweralkyl-3,4-dihydroxyphenyl propionic acid or α-hydrazino-3,4-dihydroxyphenyl propionic acid or a pharmaceutically acceptable non-toxic salt of either in combination with (B) a specific class of esters of α-methyl-3,4-dihydroxyphenylalaninate or a salt thereof.

15 Claims, No Drawings

COMPOSITIONS AND METHOD OF TREATING HYPERTENSION

BACKGROUND OF THE INVENTION

It is known in the art that α-methyl-3,4-dihydroxyphenylalaninate is useful in the treatment of antihypertensive patients (see U.S. Pat. Nos. 2,868,818 and 3,344,023). It is also known in the art that the alkyl esters of α-methyl-3,4-dihydroxyphenylalanine may be used to rapidly decrease blood pressure by parenteral administration (see U.S. Pat. No. 3,230,143). It is further known that L-α-hydrazino-α-loweralkyl-3,4-dihydroxyphenyl propionic acid or α-hydrazino-3,4-dihydroxyphenyl propionic acid potentiate the antihypertensive activity of α-methyl-3,4-dihydroxyphenylalaninate (See U.S. Pat. No. 3,462,536). It has more recently been discovered that a new class of esters of α-methyl-3,4-dihydroxyphenylalanine are particularly advantageous in combatting hypertension (see Belgium Pat. No. 820,253 published Mar. 24, 1975 or U.S. Ser. No. 482,103 filed June 25, 1974.)

OBJECTS OF THE INVENTION

It is an object of the present invention to provide a composition which more effectively treats hypertension. A further object is to provide a method of treatment which is more effective than prior art methods. A still further object is to produce a combination of drugs which is more potent than the individual components. Other objects will become apparent as the description of the invention proceeds.

THE INVENTION

These objects are accomplished by the present invention which provided a method for lowering blood pressure in an animal which comprises administering to the animal a therapeutically effective amount of a composition containing a compound (A) selected from the group consisting of L-α-hydrazino-α-loweralkyl-3,4-dihydroxyphenyl propionic acid or α-hydrazino-3,4-dihydroxyphenyl propionic acid and a pharmaceutically acceptable non-toxic salt thereof and a compound (B) having the formula:

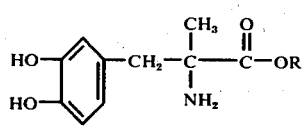

wherein
R is a radical selected from the group consisting of 2-acetamindoethyl, α-pivaloyloxyethyl and α-succinimidoethyl,
or a pharmaceutically acceptable non-toxic salt thereof.

In a preferred embodiment of the present invention, the "loweralkyl" group of compound (A) is methyl and the R radical is α-pivaloyloxyethyl or α-succinimidoethyl. In a still more preferred embodiment, the compound (B) is in the L or S stereo configuration.

The composition of the present invention may be administered in varying amounts depending upon the severity of the hypertension. In general, however, the composition is administered in amounts of from about 0.005 to about 300 mg./kg., more preferably from 0.05 to 100 mg./kg., of body weight of the animal. In a still more preferred embodiment of the present invention the composition is administered in amounts of from 0.1 to 75 mg./kg. of body weight of the animal.

The present invention further provides a pharmaceutical composition comprising an inert pharmaceutically acceptable diluent and a therapeutically effective amount of a compound (A) selected from the group consisting of L-α-hydrazino-α-loweralkyl-3,4-dihydroxyphenyl propionic acid or α-hydrazino-3,4-dihydroxyphenyl propionic acid and a pharmaceutically acceptable non-toxic salt thereof and a compound (B) having the formula:

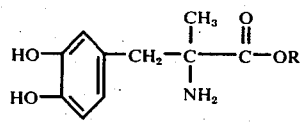

wherein
R is a radical selected from the group consisting of 2-acetamindoethyl, α-pivaloyloxyethyl and α-succinimidoethyl,
or a pharmaceutically acceptable non-toxic salt thereof.

The ratio of compound (A) to compound (B) may be varied as desired since the ratio will depend somewhat on the activity of the compounds. In general, however, the weight ratio of compound (A) to compound (B) will be from about 0.05 to about 20 and more preferably from 0.1 to 10. In a still more preferred embodiment, the weight ratio will be from 0.5 to 5.

The term "administering" merely signifies that the composition can be given to the animal by various routes. Preferably, the composition is given orally as a single pill or capsule but the i.p. or i.v. administration is also effective. Further, a penetrant such as dimethylsulfoxide may be used for topical administration of the drugs. The term "loweralkyl" is used to signify an alkyl group of from 1 to 3 carbon atoms. The expression "pharmaceutically acceptable non-toxic salt" is an expression well known in the art and includes those compounds which are made by the reaction of the free base with an inorganic or an organic acid. It includes the hydrochloride, hydrobromide, salts with sulfuric acid, oxalic acid and the like.

The terminology "inert pharmaceutically acceptable diluent" means any material which may be used as a carrier or diluent in the composition. Preferably, the compositions are administered in unit dosage form such as tablets, pills, capsules, powders, granules, sterile parenteral solutions or suspensions, oral solutions or suspensions and the like. For preparing solid compositions such as tablets, the principal active ingredient is mixed with conventional tableting ingredients such as corn starch, lactose, sucrose, sorbitol, talc, stearic acid, magnesium stearate, dicalcium phosphate, gums and fractionally similar materials as pharmaceutical diluents or carriers. The tablets or pills of the novel compositions can be laminated or otherwise compounded to provide a dosage from affording the advantage of prolonged or delayed action or predetermined successive action of the enclosed medication. For example, the table or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The compounds are also useful when administered in the form of suppositories or with a penetrant such as dimethyl sulfoxide.

The liquid forms in which the novel composition of the present invention maybe incorporated for administration include suitably flavored emulsions with edible oils such as, cottonseed oil, sesame oil, coconut oil, peanut and the like, as well as elixirs and similar pharmaceutical vehicles. Suitable dispersing or suspending agents for aqueous suspensions include synthetic and natural gums, such as, tragacanth, acacia, alginate, dextran, sodium carboxymethylcellulose, methylcellulose, polyvinylprrolidone, gelatin and the like. Sterile suspensions or solutions are required for parenteral use. Isotonic preparations containing suitable preservatives are also highly desirable for injection use.

The term single dosage form as used in the specification refers to physically discrete units suitable as unitary dosage for warm-blooded animal subjects, each unit containing a predetermined quantity of active material calculated to produce the desired therapeutic effect in association with the required pharmaceutical diluent, carrier or vehicle. The specifications for the novel single dosage forms of this invention are dictated by and are directly dependent on (a) the unique characteristics of the active material and the particular therapeutic effect to be achieved, and (b) the limitations inherent in the art of compounding such an active material for therapeutic use in warm-blooded animals as disclosed in detail in this specification. Examples of suitable oral single dosage forms in accord with this invention are tablets, capsules, pills, powder packets, granules, wafers, cachets, teaspoonfuls, dropperfuls, ampules, vials, segregated multiples of any of the foregoing, and other forms as herein described.

In a preferred embodiment of the present invention, the compound (A) is α-hydrazino-α-methyl-3,4-dihydroxyphenyl propionic acid or α-hydrazino-3,4-dihydroxyphenyl propionic acid. With the latter compound either the D or L isomers may be used as well as the racemate since both isomers are active, With the former compound, only the L isomer of the compound is active so this isomer is preferred even though the racemate could be used.

EXAMPLES 1 – 10

The following examples are given to illustrate the invention and are not intended to limit it in any manner. All parts are given in parts by weight unless otherwise expressed. In the Examples HMD signifies the compound L-α-hydrazino-α-methyl-3,4-dihydroxyphenyl propionic acid. Compound X is 2-acetamindoethyl S-3-(3,4-dihydroxyphenyl)-2-methylalaninate hydrogen oxalate monohydrate. Compound Y is α-pivaloyloxyethyl (S)-3-(3,4-dihydroxyphenyl)-2-methylalaninate hydrochloride. Compound Z is α-succinimidoethyl (S)-2-methyl-3-(3,4-dihydroxyphenyl) alaninate hydrochloride dihydrate.

The compounds are evaluated for their effect on the mean arterial pressure in conscious Wistar or Wistar-Kyoto normotensive and Wistar-Okamoto spontaneously hypertensive rats. Only male rats of 290 to 350 g body weight and 30 to 40 weeks of age are used. The catheters are implanted under ether anasthesia. The caudal artery of the rat is cannulated (approximately 1 cm beyond the anus) with the PE-10 tubing. The rostral end of the catheter is placed in the abdominal aorta just below the left renal artery. The PE-10 tubing flare and one end of the 20-g needle connector (anchor) are buried in the caudal groove of the tail and the fascia and skin sutured. The PE-60 tubing with its tubular spring guard is fastened to the 20-g needle connector (anchor) and subsequently to the water-tight swivel (above the rat cage). The swivel, in turn, is connected to a P-23Gb Statham strain gauge. Associated with the strain gauge is a 3-way stopcock and adjustable needle valve system which permits continuous, sterile, pyrogen-free, pure water infusion at a rate of approximately 5 ml/24 hours. One day is allowed for recovery from surgery before the start of treatment. The arterial pressure is recorded continuously through Statham P-23Gb transducers on a Honeywell 906C Visicorder. Means arterial pressure and heart rate data are printed at ½-hour intervals through a data acquisition system (Data Graphics Corp., San Antonio, Tex.) by means of ASR-33 teletype units.

All compounds are administered i.p. and HMD is given 5 minutes prior to the test compounds. The results are summarized in Table 1.

TABLE 1

| Examples | Treatment | Dose mg/kg i.p. | Weight ratio of compounds | No. Rats/ Group | Mean Arterial Pressure mm Hg, at Hours after Treatment | | | | | | | | |
|---|---|---|---|---|---|---|---|---|---|---|---|---|---|
| | | | | | 0 | 1/2 | 1 | 2 | 4 | 8 | 12 | 18 | 24 |
| 1 | Saline | 2 ml/kg | | 9 | 168 | 170 | 170 | 170 | 166 | 164 | 166 | 166 | 164 |
| 2 | HMD | 25 | | 6 | 167 | 166 | 164 | 166 | 158 | 167 | 172 | 172 | 162 |
| 3 | Cpd. X | 15.8 | | 10 | 160 | 151 | 156 | 154 | 151 | 154 | 151 | 157 | 164 |
| 4 | HMD | 25 | | | | | | | | | | | |
|   | Cpd. X | 15.8 | 1.58 | 4 | 164 | 151 | 138 | 127 | 124 | 127 | 127 | 130 | 124 |
| 5 | Cpd. Y | 8.9 | | 6 | 163 | 160 | 162 | 160 | 160 | 164 | 163 | 165 | 164 |
| 6 | HMD | 25 | | | | | | | | | | | |
|   | Cpd. Y | 8.9 | 2.81 | 4 | 173 | 144 | 139 | 138 | 133 | 122 | 117 | 124 | 128 |
| 7 | Cpd. Z | 9.5 | | 6 | 159 | 155 | 154 | 153 | 155 | 156 | 158 | 155 | 160 |
| 8 | HMD | 25 | | | | | | | | | | | |
|   | Cpd. Z | 9.5 | 2.63 | 4 | 157 | 148 | 137 | 135 | 123 | 119 | 125 | 124 | 128 |
| 9 | Cpd. Z | 38 | | 6 | 164 | 150 | 142 | 136 | 136 | 150 | 150 | 164 | 167 |
| 10 | HMD | 25 | | | | | | | | | | | |
|   | Cpd. Z | 38 | 0.66 | 4 | 169 | 149 | 132 | 122 | 108 | 114 | 114 | 125 | 145 |

Example 1 shows that a saline solution has essentially no effect on blood pressure. Example 2 shows that L-α-hydrazino-α-methyl-3,4-dihydroxyphenyl propionic acid by itself has essentially no effect on blood pressure. Example 3 shows that the compound 2-acetamidoethyl S-3-(3,4-dihydroxyphenyl)-2-methylalaninate hydrogen oxalate monohydrate has a moderate effect on blood pressure. Example 4 shows that the combination of L-α-hydrazino-α-methyl-3,4-dihydroxyphenyl propionic acid and 2-acetamidoethyl S-3-(3,4-dihydroxyphenyl)-2-methylalaninate hydrogen oxalate monohydrate has a substantial effect on blood pressure. Example 5 shows that the compound α-pivaloyloxyethyl (S)-3-(3,4-dihydroxyphenyl)-2-methylalaninate hydrochloride has little effect on blood pressure. Example 6 shows that the combination L-α-hydrazino-α-methyl-3,4-dihydroxyphenyl propionic acid and α-pivaloyloxyethyl (S)-3-(3,4-dihydroxyphenyl)-2-methylalaninate hydrochloride has a substantial effect on blood pressure. Example 7 shows that the compound α-succinimidoethyl (S)-2-methyl-3-(3,4-dihydroxyphenyl alaninate hydrochloride dihydrate has a moderate effect on blood pressure in the dosage indicated. Example 8 shows that the combination of L-α-hydrazino-α-methyl-3,4-dihydroxyphenyl propionic acid and α-succinimidoethyl (S)-2-methyl-3-(3,4-dihydroxyphenyl)alaninate hydrochloride dihydrate has a substantial effect on blood pressure. Example 9 shows the the compound α-succinimidoethyl (S)-2-methyl-3-(3,4-dihydroxyphenyl) alaninate hydrochloride dihydrate at a more elevated dose shows a more substantial decrease in blood pressure. Example 10 shows that the combination of L-α-hydrazino-α-methyl-3,4-dihydroxyphenyl propionic acid and α-succinimidoethyl (S)-2-methyl-3-(3,4-dihydroxyphenyl) alaninate hydrochloride dihydrate at a more elevated dosage has an even more substantial decrease in blood pressure.

When each of the above examples is repeated employing racemic α-hydrazino-α-3,4-dihydroxyphenyl propionic acid in place of the L-α-hydrazino-α-methyl-3,4-dihydroxyphenyl propionic acid, substantially the same results are obtained.

When the combination is administered orally instead of i.p. a similar reduction in blood pressure is obtained.

EXAMPLE 11

Gelatin capsules are manufactured utilizing the following composition:

| | |
|---|---|
| α-succinimidoethyl (S)-2-methyl-3-(3,4-dihydroxyphenyl) alaninate hydrochloride dihydrate | 25 mg. |
| L-α-hydrazino-α-methyl-3,4-dihydroxyphenyl propionic acid | 25 mg. |
| Mannitol | 98.5 mg. |
| Stearic acid | 1.5 mg. |

The ingredients are homogenously mixed and filled into No. 2 interlocking gelatin capsules via a capsule filling machine.

| | |
|---|---|
| Individual weight of one capsule | 150 mg. |
| Active substance content of one capsule | 50 mg. |

Many other equivalent modifications will be apparent to those skilled in the art from a reading of the foregoing without a departure from the inventive concept.

What is claimed is:
1. A method for lowering blood pressure in an animal which comprises administering to the animal a therapeutically effective amount of a composition containing a compound (A) selected from the group consisting of L-α-hydrazino-α-loweralkyl-3,4-dihydroxyphenyl propionic acid or α-hydrazino-3,4-dihydroxyphenyl propionic acid and a pharmaceutically acceptable non-toxic salt thereof and a compound (B) having the formula:

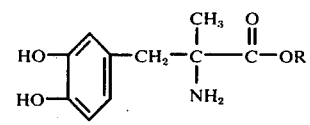

wherein
R is a radical selected from the group consisting of 2-acetamidoethyl, α-pivaloyloxyethyl and α-succinimidoethyl,
or a pharmaceutically acceptable non-toxic salt thereof, and wherein the weight ratio of (A) : (B) is from about 0.05 to about 20.

2. The method of claim 1 wherein the compound (A) is L-α-hydrazino-α-methyl-3,4-dihydroxyphenyl propionic acid.

3. The method of claim 1 wherein the compound (B) is α-succinimidoethyl (S)-2-methyl-3-(3,4-dihydroxyphenyl) alaninate.

4. The method of claim 1 wherein the compound (B) is α-pivaloxyloxyethyl (S)-3-(3,4-dihydroxyphenyl)-2-methylalaninate.

5. The method of claim 1 wherein the compound (B) is 2-acetamidoethyl S-3-(3,4-dihydroxyphenyl)-2-methylalaninate.

6. The method of claim 1 wherein the composition is administered in amounts of from about 0.005 to about 300 mg./kg. of body weight of the animal.

7. The method of claim 1 wherein the composition is administered in amount of from 0.05 to 100 mg./kg. of body weight of the animal.

8. The method of claim 1 wherein the composition is administered in amounts of from 0.1 to 75 mg./kg. of body weight of the animal.

9. A pharmaceutical composition comprising an inert pharmaceutically acceptable diluent and a therapeutically effective amount of a compound (A) selected from the group consisting of L-α-hydrazino-α-loweralkyl-3,4-dihydroxyphenyl propionic acid or α-hydrazino-3,4-dihydroxyphenyl propionic acid and a pharmaceutically acceptable non-toxic salt thereof and a compound (B) having the formula:

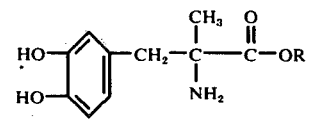

wherein
R is a radical selected from the group consisting of 2-acetamidoethyl, α-pivaloyloxyethyl and α-succinimidoethyl, or a pharmaceutically acceptable non-toxic salt thereof, and wherein the weight ratio of (A) : (B) is from about 0.05 to about 20.

10. The pharmaceutical composition of claim 9 wherein the compound (A) is L-α-hydrazino-α-methyl-3,4-dihydroxyphenyl propionic acid.

11. The pharmaceutical composition of claim 9 wherein the compound (B) is α-succinimidoethyl (S)-2-methyl-3-(3,4-dihydroxyphenyl)alaninate.

12. The pharmaceutical composition of claim 9 wherein the compound (B) is α-pivaloyloxyethyl (S)-3-(3,4-dihydroxyphenyl)-2-methylalaninate.

13. The pharmaceutical composition of claim 9 wherein the compound (B) is 2-acetamidoethyl S-3-(3,4-dihydroxyphenyl)-2-methylalaninate.

14. The pharmaceutical composition of claim 9 wherein the weight ratio of compound (A) to compound (B) is from 0.1 to 10.

15. The pharmaceutical composition of claim 9 wherein the weight ratio of compound (A) to compound (B) is from 0.5 to 5.

* * * * *